(12) United States Patent
Zhang et al.

(10) Patent No.: US 11,828,734 B2
(45) Date of Patent: Nov. 28, 2023

(54) LOADING APPARATUS FOR ROCK FRACTURING SIMULATION AND ROCK FRACTURING SIMULATION DEVICE

(71) Applicant: China University of Geosciences (Beijing), Beijing (CN)

(72) Inventors: Jinchuan Zhang, Beijing (CN); Xiwei Wang, Beijing (CN); Zhongming Li, Beijing (CN); Pei Li, Beijing (CN); Shijing Chen, Beijing (CN); Yang Liu, Beijing (CN); Xiaoliang Wei, Beijing (CN)

(73) Assignee: China University of Geosciences (Beijing), Beijing (CN)

( * ) Notice: Subject to any disclaimer, the term of this patent is extended or adjusted under 35 U.S.C. 154(b) by 378 days.

(21) Appl. No.: 17/386,360

(22) Filed: Jul. 27, 2021

(65) Prior Publication Data

US 2021/0356367 A1 Nov. 18, 2021

Related U.S. Application Data

(63) Continuation of application No. PCT/CN2020/111474, filed on Aug. 26, 2020.

(30) Foreign Application Priority Data

Dec. 31, 2019 (CN) .......................... 201911409246.3

(51) Int. Cl.
*G01N 3/08* (2006.01)
*G01N 3/06* (2006.01)
*G01N 33/24* (2006.01)

(52) U.S. Cl.
CPC ................. *G01N 3/06* (2013.01); *G01N 3/08* (2013.01); *G01N 33/24* (2013.01); *G01N 2203/0019* (2013.01); *G01N 2203/0067* (2013.01)

(58) Field of Classification Search
CPC ............ G01N 3/06; G01N 3/08; G01N 33/24; G01N 2203/0019; G01N 2203/0067; G01N 3/12; G01N 3/02; G01N 2203/0062
See application file for complete search history.

(56) References Cited

U.S. PATENT DOCUMENTS 9,880,081 B1 * 1/2018 Gupta ...................... G01N 3/24
10,634,596 B2  4/2020 Zhang et al.
(Continued)

FOREIGN PATENT DOCUMENTS

CN  203869957 U  10/2014
CN  106918531 A  7/2017
(Continued)

*Primary Examiner* — David J Bolduc
(74) *Attorney, Agent, or Firm* — AP3 Law Firm PLLC

(57) ABSTRACT

A loading apparatus for rock fracturing simulation includes an upper cover plate, a lower cover plate, lateral pressure pieces, and an acoustic measurement module top pillar. There are at least two lateral pressure pieces which are provided with a force applying face respectively for transmitting a radial force to a core sample. The upper cover plate, the lower cover plate and the lateral pressure pieces enclose a loading space for placing the core sample, and the lateral pressure pieces can slide along a radial direction of the core sample and relative to the upper cover plate or the lower cover plate. The lateral pressure pieces are provided with a sensor inserting hole for allowing a sensor to pass through respectively, and the sensor is attached to an outer peripheral wall of the core sample.

20 Claims, 7 Drawing Sheets

(56) References Cited

U.S. PATENT DOCUMENTS

2015/0168282 A1    6/2015  He et al.
2020/0018671 A1*  1/2020  Zhang .................... H04N 23/54
2021/0190755 A1*  6/2021  Martysevich ............ G01N 3/06

FOREIGN PATENT DOCUMENTS

| CN | 108952659 A | 12/2018 |
|----|-------------|---------|
| CN | 109001040 A | 12/2018 |
| CN | 209311230 U | 8/2019 |

* cited by examiner

LOADING APPARATUS FOR ROCK FRACTURING SIMULATION AND ROCK FRACTURING SIMULATION DEVICE

CROSS-REFERENCE TO RELATED APPLICATIONS

This application is a continuation application of International Application No. PCT/CN2020/111474, filed on Aug. 26, 2020, which claims priority to Chinese Patent Application No. CN 201911409246.3, filed on Dec. 31, 2019. The disclosures of the aforementioned applications are hereby incorporated herein by reference in their entireties.

TECHNICAL FIELD

The present application relates generally the technical field of rock fracturing physical simulation, and in particular, relates to a loading apparatus for rock fracturing simulation and a rock fracturing simulation device.

BACKGROUND

Recently, the development process of unconventional oil and gas such as shale gas has been accelerated. Compared with conventional oil and gas reservoirs, unconventional oil and gas reservoirs are usually more compact, more complex in pore structure, and lower in porosity and permeability, which leads to more difficulty in oil and gas production, and then restricts oil and gas recovery efficiency and extraction efficiency. At present, the industry mainly realizes the fracture production and permeability enhancement of the reservoir by a fracturing reformation technology, and then realizes efficient development of unconventional oil and gas wells. Fracturing technology has been widely used in the fields of coalbed methane, tight gas, shale gas, etc. The fracturability of reservoir rocks is recognized as an important indicator for evaluating the development value of the unconventional oil and gas reservoirs. Therefore, how to simulate the fracturing process of rock reservoirs in an all-around, true and accurate manner, obtain effective fracture parameters, and comprehensively evaluate the fracturing effect is currently the key to evaluate the unconventional oil and gas reservoir geology and development technology.

The physical simulation of rock fracturing is a method of artificially increasing the internal pressure of a rock sample in a room so as to study the fracturability of the rock and the mechanism of fracture propagation.

When the existing rock fracturing simulation or mechanical parameter testing apparatus (e.g., uniaxial, true/false triaxial, etc.) is used for fracturing simulation tests, samples are mainly artificial (e.g., cement material, etc.) specimens, cube samples, and field outcrop samples; and actual drilling cores or artificial core samples are seldom considered. However, actual drilling cylindrical cores are irreplaceable and can reflect actual formation conditions and rock properties. In addition, at present, sample loading apparatuses of the common fracturing simulation or mechanical testing apparatuses on the market are integrated with the whole machine, and most of them are not adjustable. They are usually limited to loading of samples with fixed sizes, cannot be separated from the whole machine, are not easy to clean, and inconvenient to use; and moreover, a monitoring sensor used in a fracturing simulation process cannot be attached to a core sample, resulting in distortion of monitoring data.

Based on above, it can be seen that the existing loading apparatuses for rock fracturing or mechanical parameter testing still have certain defects in the design of specific details. How to improve the loading apparatuses of rock samples on the basis of fitting actual cores of the diversified rock samples (having different outer diameters) as closely as possible is currently an important research content for improving the performance of rock fracturing simulation apparatuses and boosting oil and gas reservoir reconstruction technology.

SUMMARY

These and other problems are generally solved or circumvented, and technical advantages are generally achieved, by embodiments of the present disclosure which provide a loading apparatus for rock fracturing simulation and a rock fracturing simulation device.

Technical Problems

The present application is directed to provide a loading apparatus for rock fracturing simulation, and aims to solve or at least improve to a certain extent the technical problems that the existing apparatus for rock fracturing simulation cannot be applied to loading of rock samples having different outer diameters and the monitoring sensor cannot be attached to the core samples.

Technical Solutions

The technical solution adopted by the present application is providing a loading apparatus for rock fracturing simulation which includes an upper cover plate, a lower cover plate, at least two lateral pressure pieces and an acoustic measurement module top pillar.

The upper cover plate is arranged above a core sample to be tested for rock fracturing. The lower cover plate is arranged below the core sample. The lateral pressure pieces are arranged on an outer peripheral wall of the core sample, each lateral pressure piece being provided with a force applying face for transmitting a radial force to the core sample. The acoustic measurement module top pillar is in up-down sliding cooperation with the upper cover plate or the lower cover plate, and configured to transmit an axial force to the core sample.

The upper cover plate, the lower cover plate and the lateral pressure pieces enclose a loading space for placing the core sample, and the lateral pressure pieces slide along a radial direction of the core sample and relative to the upper cover plate or the lower cover plate.

Each lateral pressure piece is provided with at least one sensor inserting hole for allowing a sensor to pass through, and the sensor is attached to the outer peripheral wall of the core sample, and wherein the loading apparatus is detachably placed in a sample chamber which belongs to a rock fracturing simulation device.

In one embodiment, the upper cover plate is provided with a plurality of upper sliding holes along the radial direction of the core sample, and the lower cover plate is provided with a plurality of lower sliding holes along the radial direction of the core sample, and each upper sliding hole, each lower sliding hole, and each lateral pressure piece are in one-to-one correspondence. The loading apparatus for rock fracturing simulation further includes a plurality of threaded tightening components, each threaded tightening component is in one-to-one correspondence with each lateral pressure piece, an upper part of each lateral pressure piece is provided with an upper threaded hole, a lower part of each lateral pressure piece is provided with a lower threaded hole, and each threaded tightening component includes an upper threaded tightening piece which is arranged in one of the upper sliding holes in a sliding manner and is in threaded connection with the upper threaded hole, and a lower threaded tightening piece which is arranged in one of the lower sliding holes in a sliding manner and is in threaded connection with the lower threaded hole.

In one embodiment, each lateral pressure piece is of a cylindrical structure, the cylindrical structure has a set of side faces, an upper end face, and a lower end face, the set of side faces includes the force applying face and two side faces which are arranged vertically and are connected, and two sides of the force applying face are connected to the two side faces respectively.

In one embodiment, the upper end face is provided with an upper boss, the lower end face is provided with a lower boss, the upper threaded hole is arranged on the upper boss, and the lower threaded hole is arranged on the lower boss.

In one embodiment, the loading apparatus for rock fracturing simulation further includes a plurality of sensor fixing pieces, the sensor fixing pieces are mounted on the lateral pressure pieces, each of the sensor fixing pieces has at least one clamping slot for clamping the sensor, and each the clamping slot is in one-to-one correspondence with each sensor inserting hole.

In one embodiment, each sensor fixing piece includes a fixing plate, a plurality of elastic extension plates which are fixed on the fixing plate, and a plurality of abutting pieces for abutting against the outer peripheral wall of the core sample, and each abutting piece is mounted on a corresponding elastic extension plate; and the clamping slot is arranged between two adjacent elastic extension plates.

In one embodiment, each abutting piece is a spring.

In one embodiment, the acoustic measurement module top pillar includes a guide pillar and a pressure pillar which is arranged at an end of the guide pillar and located between the upper cover plate and the lower cover plate, and the lower cover plate is provided with a guide hole for the guide pillar to pass through. A lower part of the lower cover plate is provided with a guide cylinder, the guide pillar is located in the guide cylinder and can slide up and down in the guide cylinder; an outer peripheral wall of the guide cylinder is provided with at least one guide cylinder threaded hole, and the loading apparatus for rock fracturing simulation further includes a guide pillar positioning bolt which is in threaded connection with the guide cylinder threaded hole and is configured to abut against and position the guide pillar.

In one embodiment, the force applying face is an arc-shaped face.

The present application further provides a rock fracturing simulation device, including the above loading apparatus for rock fracturing simulation.

Advantageous Effects of the Disclosure

According to the loading apparatus for rock fracturing simulation, by arranging the lateral pressure pieces which can slide relative to the upper cover plate or the lower plate, the loading apparatus for rock fracturing simulation of the present application can be used to perform simulated loading tests on cylindrical core samples having different outer diameters, and at the same time, the loading apparatus for rock fracturing simulation of the present application can be independent of the rock fracturing simulation device, which facilitates loading and unloading of the core samples, and also facilitates cleaning. In addition, by providing the sensor inserting holes on the lateral pressure pieces, the problem that the sensor cannot be attached to the outer peripheral wall of core sample is solved.

According to the rock fracturing simulation device, by arranging the lateral pressure pieces which can slide relative to the upper cover plate or the lower plate, the loading apparatus for rock fracturing simulation of the present application can be used to perform simulated loading tests on cylindrical core samples having different outer diameters, and at the same time, the loading apparatus for rock fracturing simulation of the present application can be independent of the rock fracturing simulation device, which facilitates loading and unloading of the core samples, and also facilitates cleaning. In addition, by providing the sensor inserting holes on the lateral pressure pieces, the problem that the sensor cannot be attached to the outer peripheral wall of core sample is solved.

The foregoing has outlined rather broadly the features and technical advantages of the present disclosure in order that the detailed description of the disclosure that follows may be better understood. Additional features and advantages of the disclosure will be described hereinafter which form the subject of the claims of the disclosure. It should be appreciated by those skilled in the art that the conception and specific embodiment disclosed may be readily utilized as a basis for modifying or designing other structures or processes for carrying out the same purposes of the present disclosure. It should also be realized by those skilled in the art that such equivalent constructions do not depart from the spirit and scope of the disclosure as set forth in the appended claims.

Figure 1:
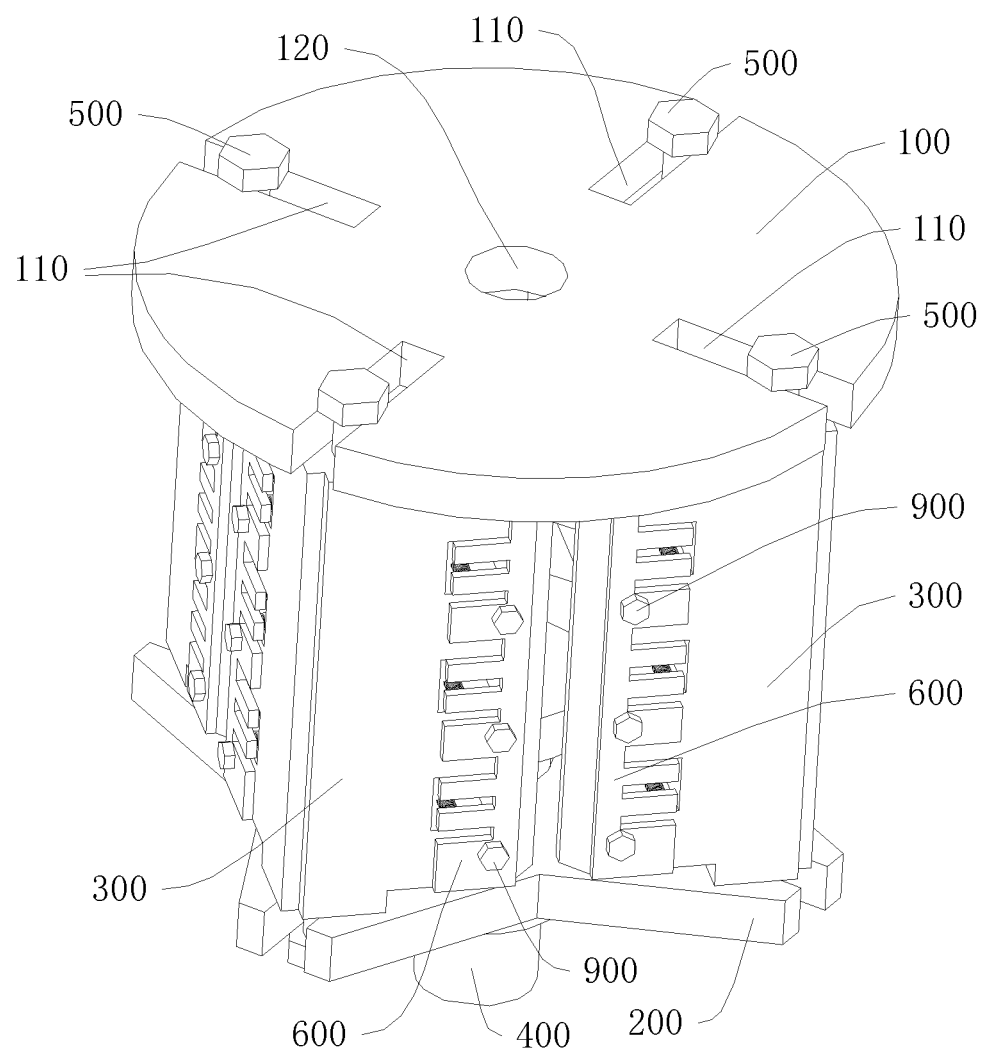
FIG. 1 is a schematic diagram I of a loading device for rock fracturing simulation according to an embodiment of the present application.

In the figures, 100: upper cover plate; 110: upper sliding hole; 120: upper through hole; 200: lower cover plate; 210: lower sliding hole; 220: guide cylinder; 300: lateral pressure piece; 310: force applying face; 320: side face; 321: fixing plate threaded hole; 330: upper end face; 331: upper boss; 3311: upper threaded hole; 340: lower end face; 341: lower boss; 3411: lower threaded hole; 350: sensor inserting hole; 400: acoustic measurement module top pillar; 410: guide pillar; 420: pressure pillar; 500: upper threaded tightening piece; 600: sensor fixing piece; 610: fixing plate; 620: elastic extension plate; 630: abutting piece; 640: clamping slot; 700: guide pillar positioning bolt; 800: lower threaded tightening piece; and 900: fixing plate bolt.

Corresponding numerals and symbols in the different figures generally refer to corresponding parts unless otherwise indicated. The figures are drawn to clearly illustrate the relevant aspects of the various embodiments and are not necessarily drawn to scale.

DETAILED DESCRIPTION OF ILLUSTRATIVE EMBODIMENTS

The making and using of the embodiments of this disclosure are discussed in detail below. It should be appreciated, however, that the concepts disclosed herein can be embodied in a wide variety of specific contexts. The specific embodiments discussed are merely illustrative, and do not limit the scope of the claims.

To make the technical problems to be solved, technical solutions, and beneficial effects of the present application clearer, the present application will be further described in detail below with reference to the accompanying drawings and embodiments. It should be understood that the specific embodiments described herein are illustrative only and are not restrictive.

It should be noted that orientations or positional relationships indicated by the terms "length", "width", "height", "thickness", "upper", "lower", "front", "rear", "left", "right", "vertical", "horizontal", "top", "bottom", "inner", "outer", "head", "tail", etc. are based on orientations or positional relationships shown in the drawings, the terms are merely for convenience in describing the present application and simplifying the description, do not indicate or imply that the apparatus or element referred to must have a specific orientation, be constructed and operated in a specific orientation, and therefore cannot be understood as a limitation of the present application.

It should also be noted that, unless otherwise clearly specified and defined, terms such as "install", "connect", "fix", and "arrange" should be understood in a broad sense. For example, it can be a fixed connection, a detachable connection, or integrated; it can be a mechanical connection, or an electrical connection; it can be a direct connection, an indirectly connection through an intermediate medium, the internal communication of two elements or an interaction relationship between two elements. Those of ordinary skill in the art can understand the specific meanings of the above terms in the application according to specific cases.

In addition, the terms "first" and "second" are only used for descriptive purposes, and cannot be understood as indicating or implying relative importance or implicitly indicating the number of indicated technical features. Thus, the features defined with "first" and "second" may explicitly or implicitly include one or more of these features. In addition, "a plurality of" and "multiple" mean two or more than two, unless otherwise specifically defined.

Referring to FIG. 1 to FIG. 6, embodiments of a loading apparatus for rock fracturing simulation will be described. The loading apparatus is detachably mounted and placed in a sample chamber, and includes an upper cover plate 100, a lower cover plate 200, lateral pressure pieces 300, and an acoustic measurement module top pillar 400.

The loading apparatus provided in the present embodiment is mainly used to perform force loading on a cylindrical core sample. There are at least two lateral pressure pieces 300 which are arranged on (e.g., by surrounding) an outer peripheral wall of the core sample, and the upper cover plate 100, the lower cover plate 200 and the lateral pressure pieces 300 enclose a loading space for placing the core sample.

Specifically, the upper cover plate 100 is arranged above the core sample, the lower cover plate 200 is arranged below the core sample, and the upper cover plate 100 and the lower cover plate 200 may abut against or cooperate in other manners with the lateral pressure pieces 300. The lateral pressure pieces 300 can slide along a radial direction of core sample and relative to the upper cover plate 100 or the lower cover plate 200, and at the same time, each lateral pressure piece 300 has a force applying face 310 for transmitting a radial force to (the outer peripheral wall of) the core sample. The acoustic measurement module top pillar 400 is in up-down sliding cooperation with the upper cover plate 100 or the lower cover plate 200, and thus the acoustic measurement module top pillar 400 can transmit an axial force to the core sample by moving up and down.

The loading apparatus for rock fracturing simulation provided in the embodiments of the present disclosure is applied to a rock fracturing simulation device, and the rock fracturing device includes a main body frame, an axial pressure mechanism, a radial pressure mechanism, and an annular confining pressure mechanism. The main body frame is provided with a sample chamber, and the loading apparatus for rock fracturing simulation provided in the embodiments of the present application is placed in the sample chamber after loading a core sample. The sample chamber itself is a placement space, the loading apparatus for rock fracturing simulation provided in the embodiments of the present application can achieve placing or removing the core sample conveniently, is an independent structure, and can be separated from the rock fracturing simulation device, which facilitates loading and unloading of core samples, and also facilitates cleaning.

A power output end of the axial pressure mechanism is connected to or abuts against the acoustic measurement module top pillar 400 to produce an axial force for loading; the radial pressure mechanism is configured to produce a horizontal radial force, the annular confining pressure mechanism is connected to a power output end of the radial pressure mechanism and applies a radial force on each lateral pressure piece 300 along a radial direction of the core sample. The structure and use method of the main body frame, the axial pressure mechanism, the radial pressure mechanism, and the annular confining pressure mechanism of the rock fracturing simulation device are all described in the prior art, and will not be repeated here.

Because the lateral pressure piece 300 has the force applying face 310, the force applying face 310 can perform radial force loading on core samples having different outer diameters, and the force applying face 310 may be a V-shaped groove face, a flat face or an arc-shaped face. Moreover, the lateral pressure piece 300 can slide along the radial direction of the core sample and relative to the upper cover plate 100 or the lower cover plate 200 (that is, the core sample), and thus the loading apparatus for rock fracturing simulation provided in the embodiments of the present application can be used to perform radial force loading on core samples of a variety of specifications (outer diameter).

In addition, the lateral pressure piece 300 is provided with at least one sensor inserting hole 350 for allowing a sensor to pass through and to be attached to the outer peripheral wall of the core sample. Because a strain sensor, an acoustic sensor, etc. are required for real-time monitoring during fracturing simulation, the lateral pressure piece 300 is provided with the sensor inserting hole 350, and the sensor inserting hole 350 is a through hole penetrating through the lateral pressure piece 300, which facilitates the mounting of each sensor which can be attached to the core sample from an outer side of the loading apparatus for rock fracturing simulation provided in the embodiments of the present application after the apparatus is assembled. By providing the sensor inserting holes 350 on the lateral pressure pieces 300, the problem that the sensor cannot be attached to the outer peripheral wall of the core sample because it may interfere with the lateral pressure piece 300 is solved.

According to the loading apparatus for rock fracturing simulation provided in the embodiments of the present application, compared with the prior art, by arranging the lateral pressure pieces 300 which can slide relative to the upper cover plate 100 or the lower cover plate 200, the loading apparatus for rock fracturing simulation provided in the embodiments of the present application can be used to perform simulated loading tests on cylindrical core samples having different outer diameters, and at the same time, the loading apparatus for rock fracturing simulation can be independent of the rock fracturing device, which facilitates loading and unloading of the core samples, and also facilitates cleaning. In addition, by providing the sensor inserting holes 350 on the lateral pressure pieces 300, the problem that the sensor cannot be attached to the outer peripheral wall of core sample is solved.

Referring to FIG. 1 to FIG. 6, as a specific embodiment of the loading apparatus for rock fracturing simulation provided in the present application, the upper cover plate 100 is provided with a plurality of upper sliding holes no which are arranged along the radial direction of the core sample, and the lower cover 200 is provided with a plurality of lower sliding holes 210 which are arranged along the radial direction of the core sample. Each upper sliding hole no, each lower sliding hole 210 and the each lateral pressure piece 300 are in one-to-one correspondence, that is, one lateral pressure piece 300 corresponds to one upper sliding hole no located above and one lower sliding hole 210 located below, respectively.

The loading apparatus for rock fracturing simulation provided in the embodiments of the present application further includes a plurality of threaded tightening components. Similarly, each set of threaded tightening components corresponds to one lateral pressure piece 300, and at the same time, each set of threaded tightening components corresponds to one upper sliding hole no and one lower sliding hole 210. An upper part of each lateral pressure piece 300 is provided with an upper threaded hole 3311, and a lower part of each lateral pressure piece 300 is provided with a lower threaded hole 3411.

Each threaded tightening component includes an upper threaded tightening piece 500 which is arranged in the corresponding upper sliding hole no in a sliding manner and is in threaded connection with the upper threaded hole 3311 of the corresponding lateral pressure piece 300 and a lower threaded tightening piece 800 which is arranged in the corresponding lower sliding hole 210 in a sliding manner and is in threaded connection with the lower threaded hole 3411 of the corresponding lateral pressure piece 300.

When the loading apparatus for rock fracturing simulation provided in the embodiments of the present disclosure loads a core sample, the core sample can be placed at an approximate central position of the lower cover plate 200, the lower part of each lateral pressure piece 300 is placed on the cover plate 200 in an abutting manner, and the upper cover plate 100 is placed on the upper part of each lateral pressure piece 300 in an abutting manner. At the moment, the upper threaded hole 3311 of the lateral pressure piece 300 is adjusted to align with the corresponding upper sliding hole no, the lower threaded hole 3411 of the lateral pressure piece 300 is adjusted to align with the corresponding lower sliding hole 210, and the force applying face 310 of each lateral pressure piece 300 is adjusted to abut against the outer peripheral wall of the core sample. Then, a screw of the upper threaded tightening piece 500 passes through the upper sliding hole no and is tightened with the upper threaded hole 3311, a screw of the lower threaded tightening piece 800 passes through the lower sliding hole 210 and is tightened with the lower threaded hole 3411, a head of the upper threaded tightening piece 500 abuts against an upper part of the upper cover plate 100, and a head of the lower threaded tightening piece 800 abuts against a lower part of the lower cover plate 200. At the moment, each lateral pressure piece 300 is positioned, and the lateral pressure pieces 300 are connected to the upper cover plate 100 and the lower cover plate 200, that is, the loading apparatus for rock fracturing simulation provided in the embodiments of the present application is assembled, and the core sample to be tested is positioned and loaded in the loading apparatus for rock fracturing simulation provided in the embodiments of the present application.

In addition, during the simulated fracturing test, annular confining pressure mechanism will make each lateral pressure piece 300 move towards a central axial line of the core sample along the radial direction of the core sample. At the moment, the upper threaded tightening piece 500 slides in the upper sliding hole 110, the lower threaded tightening piece 800 slides in the lower sliding hole 210, and the cooperation of upper threaded tightening piece 500 and the upper sliding hole no and the cooperation of the lower threaded tightening piece 800 and the lower sliding hole 210 play a role in guiding the movement of the lateral pressure pieces 300 to a certain extent.

As s specific embodiment of the loading apparatus for rock fracturing simulation provided in the present application, the upper threaded tightening piece 500 and the lower threaded tightening piece 800 may be a bolt or screw.

Referring to FIG. 1 to FIG. 4 and FIG. 7, as a specific embodiment of the loading apparatus for rock fracturing simulation provided in the present application, the loading apparatus for rock fracturing simulation provided in the embodiments of the present application further includes a plurality of sensor fixing pieces 600. The sensor fixing pieces 600 are mounted on the lateral pressure pieces 300, and one lateral pressure piece 300 may be provided with one sensor fixing piece 600 or multiple sensor fixing pieces 600.

Each sensor fixing piece 600 has at least one clamping slot 640 for mounting the sensor in a clamping manner, and each clamping slot 640 corresponds to one sensor inserting hole 350. The sensor is fixed on the sensor fixing piece 600 in a clamping manner, and the fixed sensor passes through the corresponding sensor inserting hole 350 and is attached to the core sample.

Referring to FIG. 1 to FIG. 4 and FIG. 7, as a specific embodiment of the loading apparatus for rock fracturing simulation provided in the present application, each sensor fixing piece 600 includes a fixing plate 610, a plurality of elastic extension plates 620 which are fixed on the fixing plate 610, and a plurality of abutting pieces 630 for abutting against the outer peripheral wall of the core sample, and one extension plate 620 is provided with at least one abutting piece 630. The clamping slot 640 is arranged between two adjacent elastic extension plates 620.

The fixing plate 610 is a main body of the sensor fixing piece 600, and the fixing plate 610 is also of a thin plate structure. The elastic extension plates 620 are long strip-shaped plates arranged on the fixing plate 610, which have certain flexibility or elasticity and can be bent and elastically deform relative to the fixing plate 610. The clamping slot 640 for mounting the sensor in a clamping manner is arranged between two adjacent elastic extension plates 620.

After the loading apparatus for rock fracturing simulation provided in the embodiments of the present application (the sensor fixing pieces 600 are also mounted on the lateral pressure pieces 300) is assembled, the clamping slot 640 is correspondingly arranged on an outer side of the sensor inserting hole 350, and at the same time, an end of the abutting piece 630 on the elastic extension 620 extends into the sensor inserting hole 350 and can abut against the outer peripheral wall of the core sample when the core sample is cracked. An operator clamps the sensor in the clamping slot 640, positions where the elastic extension plates 620 are arranged can ensure the clamped sensor to be attached to the outer peripheral wall of the core sample.

During the simulated fracturing of the core sample, the core sample may be cracked, if the monitoring sensor which is tightly attached to the core sample is fixed on the lateral pressure piece 300 or is fixed between the lateral pressure piece 300 and the core sample, an impact force produced by the cracking of the core sample may break down the expensive sensor. To avoid this problem, the above sensor fixing pieces 600 are specially arranged. The sensor is fixed between the adjacent elastic extension plates 620 in a clamping manner, if the core sample is not cracked, the sensor is attached to the outer peripheral wall of the core sample all the time, during the cracking of the core sample, the abutting pieces 630 will move towards the outer side away from the center of the core sample under the action of the core sample, because the elastic extension plates 620 can be bent and elastically deform relative to the fixing plate 610, the elastic extension plates 620 and the sensor can move towards the outer side along with the abutting pieces 630 at the same time, and thus the sensor is protected from being broken down by the core sample.

Referring to FIG. 1 to FIG. 4 and FIG. 7, as a specific embodiment of the loading apparatus for rock fracturing simulation provided in the present application, the fixing plate 610 is in threaded connection with the lateral pressure piece 300. Specifically, the fixing plate 610 is provided with a fixing plate through hole, the lateral pressure piece 300 is provided with a fixing plate threaded hole 321, the loading apparatus for rock fracturing simulation provided in the embodiments of the present application further includes a fixing plate bolt 900, a screw of the fixing plate bolt 900 passes through the fixing plate through hole and is in threaded connection with the fixing plate threaded hole 321, and thus the fixing plate 610 is fixedly connected to the lateral pressure piece 300.

Figure 7:
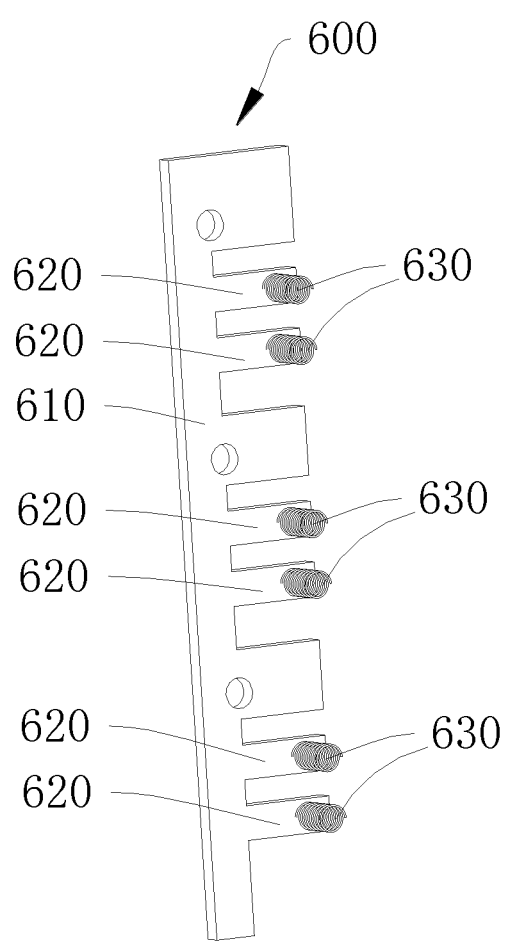
FIG. 7 is a schematic diagram of a sensor fixing piece in FIG. 4.

Referring to FIG. 7, as a specific embodiment of the loading apparatus for rock fracturing simulation provided in the present application, each abutting piece 630 is a spring. One end of the spring is connected to the elastic extension plate 620, and the other end of the spring is configured to abut against the core sample. The spring has compressibility, due to possible slight vibration or jitter in the simulated fracturing test, the spring can buffer part of the vibration and jitter to protect the sensor. The elastic modulus of the spring is higher than that of the elastic extension plate 620, that is, the rigidity of the spring is lower than that of the elastic extension plate 620. Thus, when the core sample vibrates and jitters slightly, these slight jitters or vibrations will be absorbed by the spring, and the elastic extension plates 620 hardly deform, so that the sensor is attached to the core sample all the time and is prevented from being separated from the core sample due to some small jitters. Only when the core sample violently deforms such as cracking, and the spring is compressed to a certain degree, the spring will drive the elastic extension plates 620 to deform to protect the sensor.

Figure 2:
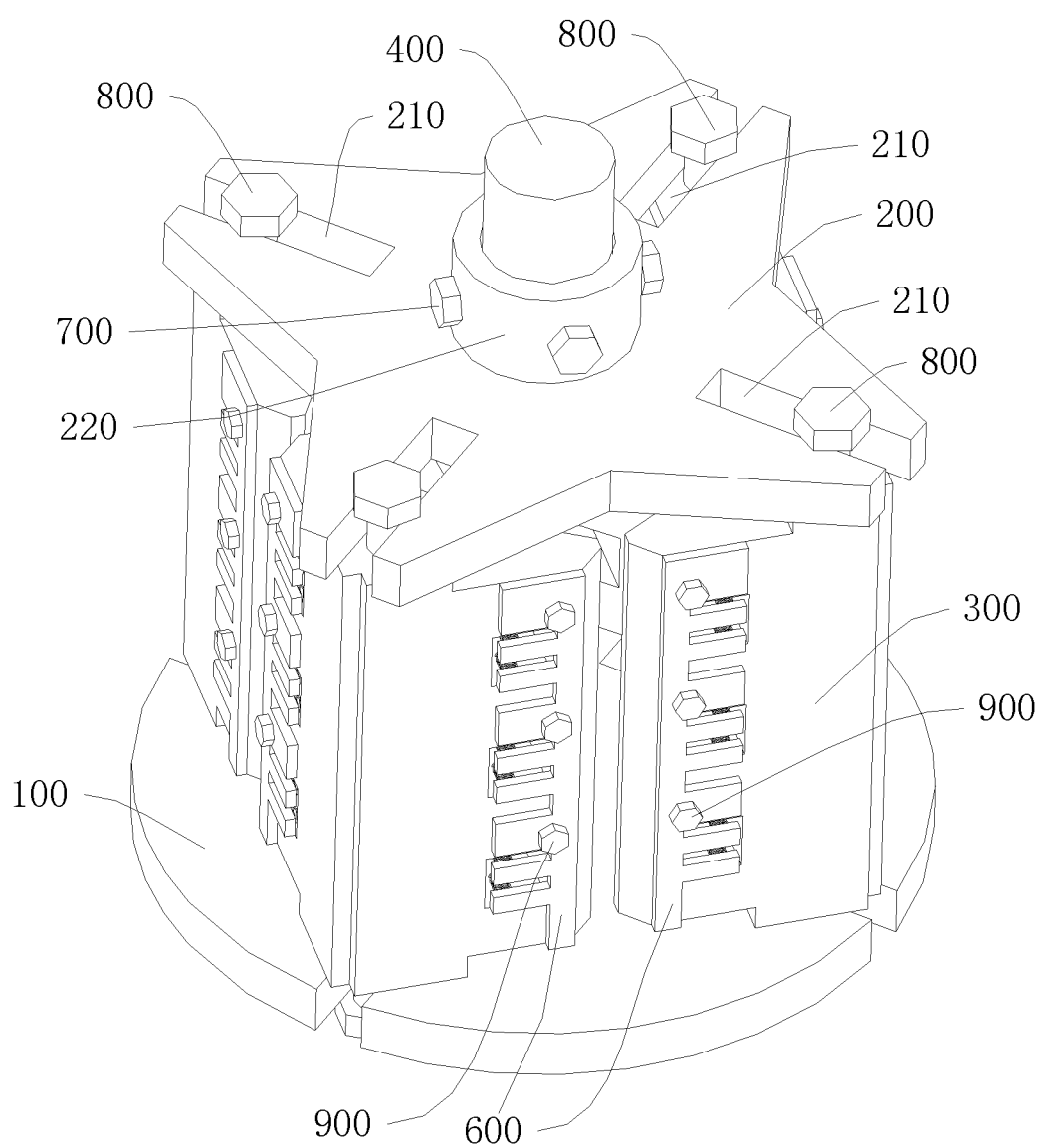
FIG. 2 is a schematic diagram II of the loading device in FIG. 1 for rock fracturing simulation according to an embodiment of the present application.
Figure 3:
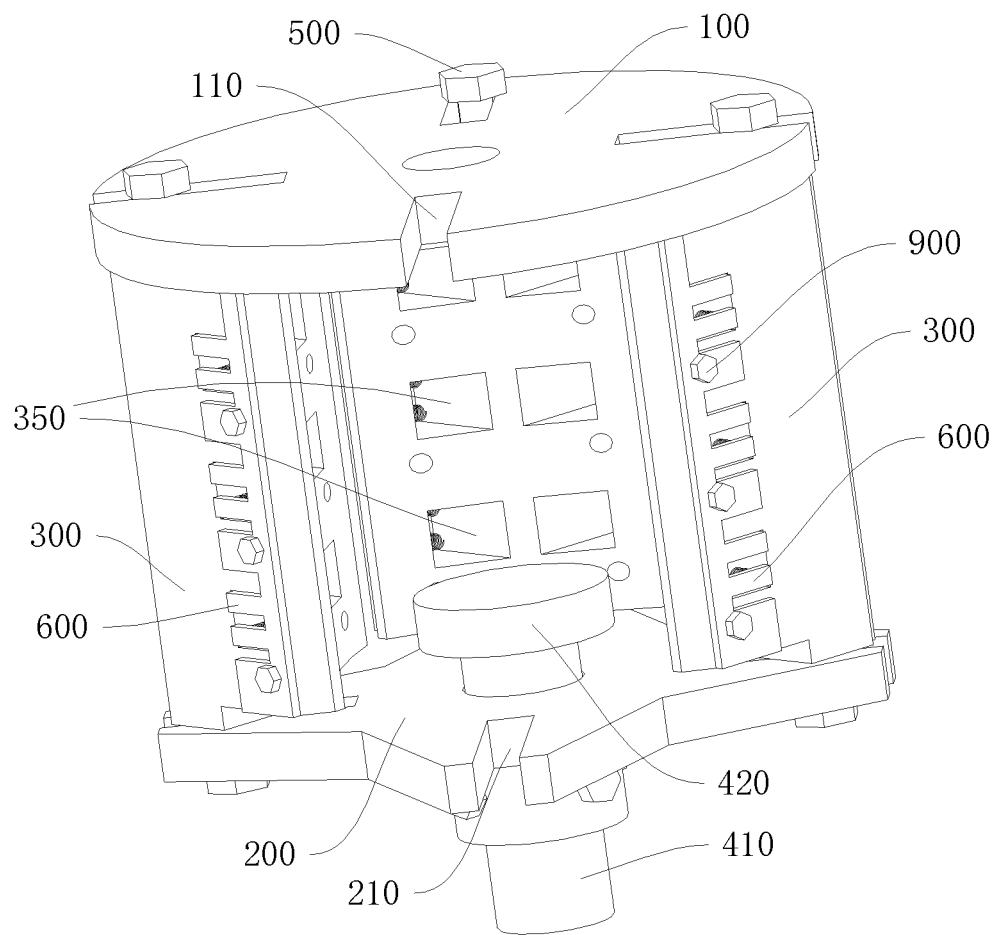
FIG. 3 is a schematic diagram of the loading device for rock fracturing simulation after one lateral pressure piece, a corresponding upper threaded tightening piece and lower threaded tightening piece are removed according to an embodiment of the present application.

Referring to FIG. 1 to FIG. 3, as a specific embodiment of the loading apparatus for rock fracturing simulation provided in the present application, there are four lateral pressure pieces 300 which are uniformly arranged around the core sample.

Referring to FIG. 1 to FIG. 6, as a specific embodiment of the loading apparatus for rock fracturing simulation provided in the present application, the lateral pressure piece 300 is of a cylindrical structure which is similar to a "chamfered structure" of a cuboid, the lateral pressure piece 300 has a set of side faces, an upper end face 330, and a lower end face 340, the set of side faces includes two side faces 320 which are arranged vertically and are connected, and the force applying face 310, and two sides of the force applying face 310 are connected to the two side faces 320, respectively.

Figure 4:
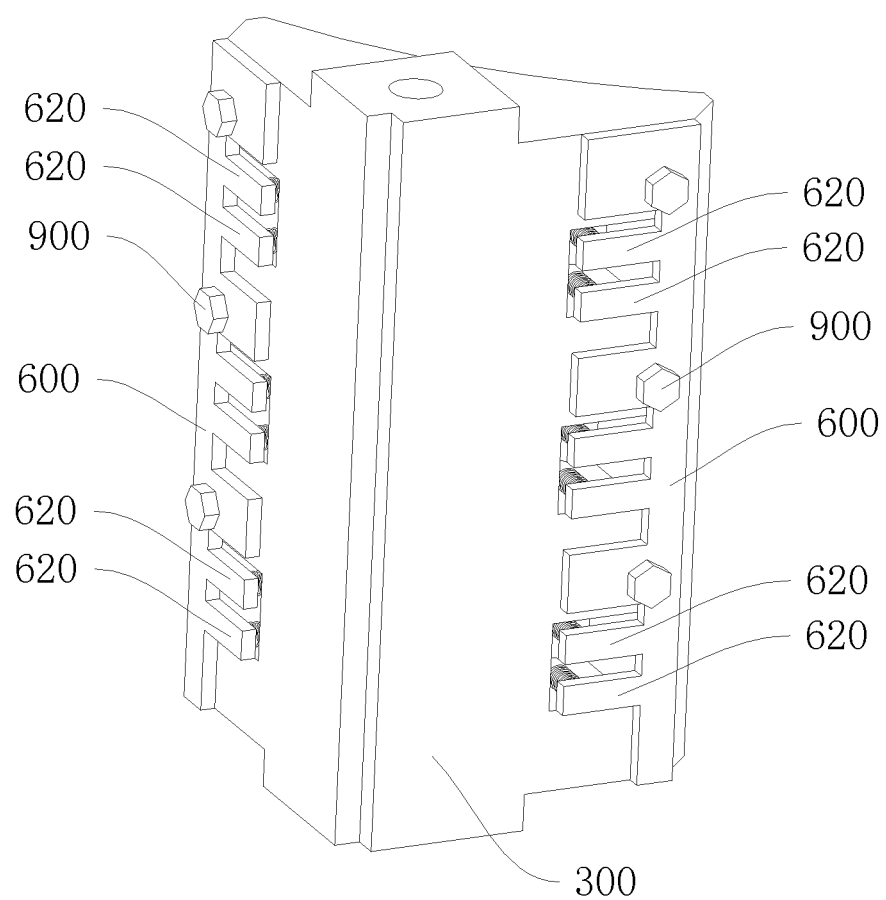
FIG. 4 is a schematic diagram of cooperation of a lateral pressure piece in FIG. 1 and a sensor fixing piece.
Figure 5:
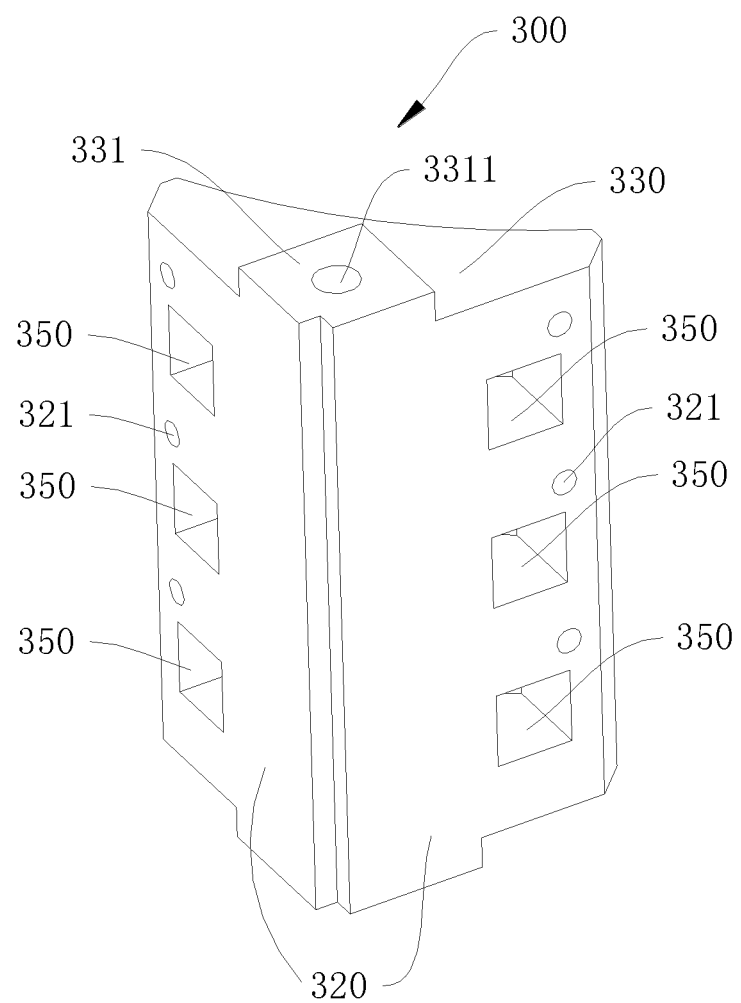
FIG. 5 is a schematic diagram I of the lateral pressure piece in FIG. 4.

Referring to FIG. 4 and FIG. 5, as a specific embodiment of the loading apparatus for rock fracturing simulation provided in the present application, the two side faces 320 are provided with three sensor inserting holes 350 which are arranged in columns and at intervals, respectively. Two side faces of one lateral pressure piece 300 are provided with one sensor fixing piece 600, respectively, the sensor fixing piece 600 is correspondingly provided with three clamping slots 640, and one clamping slot 640 corresponds to one sensor inserting hole 350.

Figure 6:
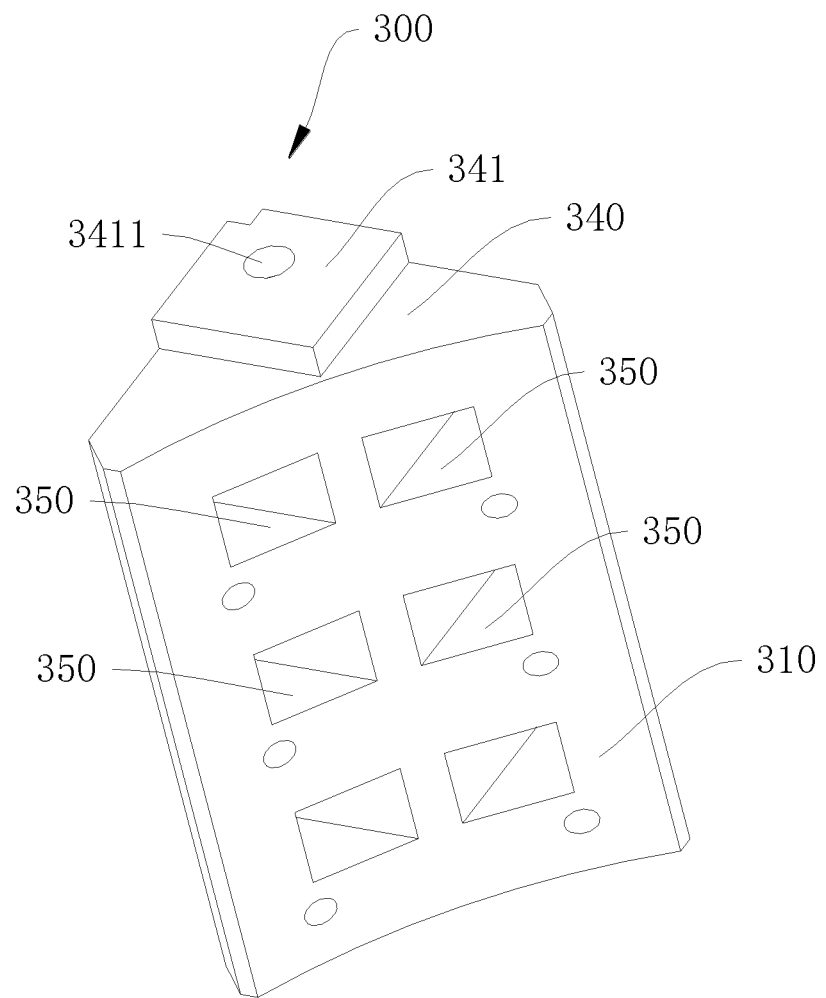
FIG. 6 is a schematic diagram II of the lateral pressure piece in FIG. 4.

Referring to FIG. 5 and FIG. 6, as a specific embodiment of the loading apparatus for rock fracturing simulation provided in the present application, the upper end face 330 of the lateral pressure piece 300 is provided with an upper boss 331, the lower end face 340 is provided with a lower boss 341, the upper threaded hole 3311 is arranged on the upper boss 331, and the lower threaded hole 3411 is arranged on the lower boss 341. The upper boss 331 abuts against a lower plate face of the upper cover plate 100, the lower boss 341 abuts against an upper plate face of the lower cover plate 200, an upper surface area of the upper boss 331 is smaller than that of the upper end face 330, a lower surface area of the lower boss 341 is smaller than that of the lower end face 340, so that when the lateral pressure pieces 300 move relative to the upper cover plate 100 or the lower cover plate 200, sliding friction forces between the lateral pressure pieces 300 and the upper cover plate 100 or the lower cover plate 200 can be reduced.

Referring to FIG. 3, as a specific embodiment of the loading apparatus for rock fracturing simulation provided in the present application, the acoustic measurement module top pillar 400 includes a guide pillar 410 and a pressure pillar 420 which is arranged on an end of the guide pillar 410, and the lower cover plate 200 is provided with a guide hole for allowing the guide pillar 410 to pass through. The pressure pillar 420 is arranged between the upper cover plate wo and the lower cover plate 200, and is configured to apply an axial force to the core sample, and the guide pillar 410 is connected to a power output end of the axial pressure mechanism and slides up and down in the guide hole.

Referring to FIG. 2 and FIG. 3, as a specific embodiment of the loading apparatus for rock fracturing simulation provided in the present application, the lower part of the lower cover plate 200 is provided with a guide cylinder 220, and the guide pillar 410 is located in the guide cylinder 220 and can slide up and down in the guide cylinder 220. The guide cylinder 220 can provide better guiding for the up-down movement of the guide pillar 410.

Referring to FIG. 2 and FIG. 3, as a specific embodiment of the loading apparatus for rock fracturing simulation provide in the present application, an outer peripheral wall of the guide cylinder 220 is provided with at least one guide cylinder threaded hole, and the loading apparatus for rock fracturing simulation provided in the embodiments of the present application further includes a guide pillar positioning bolt 700 which is in threaded connection with the guide cylinder threaded hole and is configured to abut against and position the guide pillar 410. A clearance is reserved between the guide pillar 410 and the guide cylinder 220 as well as the guide hole, by arranging the guide pillar positioning bolt 700, the positions of the guide pillar 410 in the guide cylinder 220 and the guide hole can be adjusted, which facilitates the adjustment and substantial coincidence of a central axial line of the pressure pillar 420 with a central axial line of the core sample. At the same time, the guide cylinder positioning bolt 700 can abut against the guide pillar 410 to pre-fix the guide pillar 410 on the lower cover plate 200, which facilitates the subsequent connection of the guide pillar 410 and the power output end of the axial pressure mechanism.

Referring to FIG. 1 and FIG. 3, as a specific embodiment of the loading apparatus for rock fracturing simulation provided in the present application, the upper cover plate 100 is further provided with an upper through hole 120, which facilitates the pouring of a fracturing fluid into a fabrication hole of the core sample in the fracturing simulation test.

Referring to FIG. 6, as a specific embodiment of the loading apparatus for rock fracturing simulation provided in the present application, the force applying face is an arc-shaped face 310. The arc-shaped face 310 can provide a face contact to a cylindrical core sample of an adaptive size, and provide a line contact to a cylindrical core sample of a non-adaptive size. In a word, the arc-shaped face 310 can provide radial forces required by the simulated fracturing to cylindrical core samples of different specifications.

The present application further provides a rock fracturing simulation device, including the loading apparatus for rock fracturing simulation in the above embodiments.

According to the rock fracturing simulation device, compared with the prior art, the loading apparatus is independent of a main body frame, which facilitates loading and unloading of the core samples, and also facilitates cleaning. At the same time, the lateral pressure pieces 300 which can slide relative to the upper cover plate 100 or the lower cover plate 200 are arranged in the loading apparatus for rock fracturing simulation, and thus the present device can be used to perform simulated loading tests on cylindrical core samples having different outer diameters. In addition, by arranging the sensor inserting hole 350 on the lateral pressure piece 300, the problem that the sensor cannot be attached to the outer peripheral wall of the core sample is solved.

As a specific embodiment of the rock fracturing simulation device provided in the present application, the rock fracturing simulation device provided in the embodiments of the present application further includes a main body frame, an axial pressure mechanism, a radial pressure mechanism, and an annular confining pressure mechanism. The axial pressure mechanism, the radial pressure mechanism and the annular confining pressure mechanism are all mounted on the main body frame, the main body frame is provided with a sample chamber, and the loading apparatus for rock fracturing simulation is placed in the sample chamber after loading a core sample.

The above are only optional embodiments of the present application and not intended to limit the present application. Any modification, equivalent replacement, improvement and the like made within the spirit and principle of the present application shall fall within the scope of protection of the present application.

Although embodiments of the present disclosure have been described in detail, it should be understood that various changes, substitutions and alterations can be made herein without departing from the spirit and scope of the disclosure as defined by the appended claims.

Moreover, the scope of the present disclosure is not intended to be limited to the particular embodiments described here. As one of ordinary skill in the art will readily appreciate from the disclosure of the present disclosure that processes, machines, manufacture, compositions of matter, means, methods, or steps, presently existing or later to be developed, may perform substantially the same function or achieve substantially the same result as the corresponding embodiments described herein. Accordingly, the appended claims are intended to include within their scope such processes, machines, manufacture, compositions of matter, means, methods, or steps.

What is claimed is:

1. A loading apparatus for rock fracturing simulation, comprising:
   an upper cover plate, arranged above a core sample to be tested for rock fracturing;
   a lower cover plate, arranged below the core sample;
   at least two lateral pressure pieces, arranged on an outer peripheral wall of the core sample, each lateral pressure piece of the at least two lateral pressure pieces being provided with a force applying face for transmitting a radial force to the core sample; and
   an acoustic measurement module top pillar, in up-down sliding cooperation with the upper cover plate or the lower cover plate, and configured to transmit an axial force to the core sample; and
   wherein the upper cover plate, the lower cover plate and the at least two lateral pressure pieces enclose a loading space for placing the core sample, and the at least two lateral pressure pieces slidable along a radial direction of the core sample and relative to the upper cover plate or the lower cover plate; and
   wherein each lateral pressure piece is further provided with at least one sensor inserting hole for allowing a sensor to pass through, and the sensor is attachable to the outer peripheral wall of the core sample, and wherein the loading apparatus is detachably placed in a sample chamber of a rock fracturing simulation device.

2. The loading apparatus for rock fracturing simulation of claim 1, wherein the upper cover plate is provided with a plurality of upper sliding holes along the radial direction of the core sample, and the lower cover plate is provided with a plurality of lower sliding holes along the radial direction of the core sample; and
   wherein the loading apparatus for rock fracturing simulation further includes a plurality of threaded tightening components, each threaded tightening component is in one-to-one correspondence with each lateral pressure piece, an upper part of each lateral pressure piece is provided with an upper threaded hole, a lower part of each lateral pressure piece is provided with a lower threaded hole, and each threaded tightening component includes an upper threaded tightening piece that is arranged in an upper sliding hole in a sliding manner and is in threaded connection with the upper threaded hole, and a lower threaded tightening piece that is arranged in a lower sliding hole in a sliding manner and is in threaded connection with the lower threaded hole.

3. The loading apparatus for rock fracturing simulation of claim 2, wherein each lateral pressure piece is of a cylindrical structure, the cylindrical structure has a set of side faces, an upper end face and a lower end face, the set of side faces comprises the force applying face and two side faces that are arranged vertically and are connected, and two sides of the force applying face are connected to the two side faces, respectively.

4. The loading apparatus for rock fracturing simulation of claim 3, wherein the upper end face is provided with an upper boss, the lower end face is provided with a lower boss, the upper threaded hole is arranged on the upper boss, and the lower threaded hole is arranged on the lower boss.

5. The loading apparatus for rock fracturing simulation of claim 4, further comprising:
a plurality of sensor fixing pieces, wherein the plurality of sensor fixing pieces are mounted on the at least two lateral pressure pieces, each of the plurality of sensor fixing pieces has at least one clamping slot for clamping the sensor, and each of the at least one clamping slot is in one-to-one correspondence with each sensor inserting hole.

6. The loading apparatus for rock fracturing simulation of claim 5, wherein each sensor fixing piece comprises a fixing plate, a plurality of elastic extension plates that are fixed on the fixing plate, and a plurality of abutting pieces for abutting against the outer peripheral wall of the core sample, each abutting piece being mounted on a corresponding elastic extension plate; and wherein the at least one clamping slot is arranged between two adjacent elastic extension plates.

7. The loading apparatus for rock fracturing simulation of claim 6, wherein each abutting piece is a spring.

8. The loading apparatus for rock fracturing simulation of claim 4, wherein: the acoustic measurement module top pillar comprises a guide pillar, and a pressure pillar that is arranged on an end of the guide pillar and located between the upper cover plate and the lower cover plate;
the lower cover plate is provided with a guide hole for allowing the guide pillar to pass through;
a lower part of the lower cover plate is provided with a guide cylinder, the guide pillar is located in the guide cylinder and slidable up and down in the guide cylinder;
an outer peripheral wall of the guide cylinder is provided with at least one guide cylinder threaded hole; and
the loading apparatus for rock fracturing simulation further comprises a guide pillar positioning bolt that is in threaded connection with the at least one guide cylinder threaded hole and is configured to abut against and position the guide pillar.

9. The loading apparatus for rock fracturing simulation of claim 4, wherein the force applying face is an arc-shaped face.

10. The loading apparatus for rock fracturing simulation of claim 3, further comprising:
a plurality of sensor fixing pieces, wherein the plurality of sensor fixing pieces are mounted on the at least two lateral pressure pieces, each of the plurality of sensor fixing pieces has at least one clamping slot for clamping the sensor, and each of the at least one clamping slot is in one-to-one correspondence with each sensor inserting hole.

11. The loading apparatus for rock fracturing simulation of claim 10, wherein each sensor fixing piece comprises a fixing plate, a plurality of elastic extension plates that are fixed on the fixing plate, and a plurality of abutting pieces for abutting against the outer peripheral wall of the core sample, each abutting piece being mounted on a corresponding elastic extension plate; and wherein the at least one clamping slot is arranged between two adjacent elastic extension plates.

12. The loading apparatus for rock fracturing simulation of claim 11, wherein each abutting piece is a spring.

13. The loading apparatus for rock fracturing simulation of claim 3, wherein:
the acoustic measurement module top pillar comprises a guide pillar, and a pressure pillar that is arranged on an end of the guide pillar and located between the upper cover plate and the lower cover plate;
the lower cover plate is provided with a guide hole for allowing the guide pillar to pass through;
a lower part of the lower cover plate is provided with a guide cylinder, the guide pillar is located in the guide cylinder and slidable up and down in the guide cylinder;
an outer peripheral wall of the guide cylinder is provided with at least one guide cylinder threaded hole; and
the loading apparatus for rock fracturing simulation further comprises a guide pillar positioning bolt that is in threaded connection with the at least one guide cylinder threaded hole and is configured to abut against and position the guide pillar.

14. The loading apparatus for rock fracturing simulation of claim 3, wherein the force applying face is an arc-shaped face.

15. The loading apparatus for rock fracturing simulation of claim 2, further comprising:
a plurality of sensor fixing pieces, wherein the plurality of sensor fixing pieces are mounted on the at least two lateral pressure pieces, each of the plurality of sensor fixing pieces has at least one clamping slot for clamping the sensor, and each of the at least one clamping slot is in one-to-one correspondence with each sensor inserting hole.

16. The loading apparatus for rock fracturing simulation of claim 15, wherein each sensor fixing piece comprises a fixing plate, a plurality of elastic extension plates that are fixed on the fixing plate, and a plurality of abutting pieces for abutting against the outer peripheral wall of the core sample, each abutting piece being mounted a corresponding elastic extension plate; and wherein the at least one clamping slot is arranged between two adjacent elastic extension plates.

17. The loading apparatus for rock fracturing simulation of claim 16, wherein each abutting piece is a spring.

18. The loading apparatus for rock fracturing simulation of claim 2, wherein:
the acoustic measurement module top pillar comprises a guide pillar, and a pressure pillar that is arranged on an end of the guide pillar and located between the upper cover plate and the lower cover plate;
the lower cover plate is provided with a guide hole for allowing the guide pillar to pass through;
a lower part of the lower cover plate is provided with a guide cylinder, the guide pillar is located in the guide cylinder and slidable up and down in the guide cylinder;

an outer peripheral wall of the guide cylinder is provided with at least one guide cylinder threaded hole; and the loading apparatus for rock fracturing simulation further comprises a guide pillar positioning bolt that is in threaded connection with the at least one guide cylinder threaded hole and is configured to abut against and position the guide pillar.

19. The loading apparatus for rock fracturing simulation of claim 2, wherein the force applying face is an arc-shaped face.

20. A rock fracturing simulation device, comprising a loading apparatus for rock fracturing simulation, the loading apparatus detachably placed in a sample chamber of the rock fracturing simulation device and comprising:

an upper cover plate, arranged above a core sample to be tested for rock fracturing;

a lower cover plate, arranged below the core sample;

at least two lateral pressure pieces, arranged on an outer peripheral wall of the core sample, each lateral pressure piece of the at least two lateral pressure pieces being provided with a force applying face for transmitting a radial force to the core sample; and an acoustic measurement module top pillar, in up-down sliding cooperation with the upper cover plate or the lower cover plate, and configured to transmit an axial force to the core sample; and wherein the upper cover plate, the lower cover plate and the at least two lateral pressure pieces enclose a loading space for placing the core sample, and the at least two lateral pressure pieces slidable along a radial direction of the core sample and relative to the upper cover plate or the lower cover plate; and wherein each lateral pressure piece is further provided with at least one sensor inserting hole for allowing a sensor to pass through, and the sensor is attachable to the outer peripheral wall of the core sample.

* * * * *